United States Patent [19]

Pryce et al.

[11] Patent Number: 5,110,957

[45] Date of Patent: May 5, 1992

[54] PROCESS FOR PREPARING 1,3-DIOXOLANE KETONES

[75] Inventors: Robert J. Pryce, Faversham; John E. Hawes, Sittingbourne; Sheetal Handa, Milton Regis, all of England

[73] Assignee: Shell Research Limited, England

[21] Appl. No.: 568,851

[22] Filed: Aug. 17, 1990

[30] Foreign Application Priority Data

Aug. 17, 1989 [GB] United Kingdom ............... 8918806

[51] Int. Cl.⁵ .................................... C07D 317/26
[52] U.S. Cl. .................................... 549/450; 549/448
[58] Field of Search .......................... 549/450

[56] References Cited

FOREIGN PATENT DOCUMENTS 244912 11/1987 European Pat. Off. .

OTHER PUBLICATIONS

Jurczak, Tetrahedron, vol. 42, (2), (1986), pp. 447–488.
Baer, Biochem. Prep., vol. 2, (1952), pp. 31–37.
Mori, Tetrahedron, vol. 32, (1976), pp. 1979–1981.
Hagen, Tetrahedron, vol. 35, (1979), pp. 2583–2589.
Hagen, Tetrahedron, vol. 36, (1980), pp. 3101–3105.
Larcheveque, Synthesis 1986, pp. 60–64.

Primary Examiner—Nicky Chan

[57] ABSTRACT

A process for preparing a ketone of the general formula:

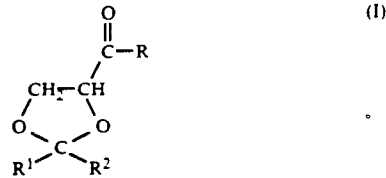

in which $R^1$ and $R^2$ each independently represent a $C_{1-6}$ alkyl or $C_{6-12}$ aryl group, and R represents an alkyl, aryl, aralkyl, heterocyclic or carboxylic group, which process comprises reacting a carboxylic acid having the general formula I in which R represents a hydroxy group with a lithium compound to form the corresponding lithium salt of the carboxylic acid; reacting the lithium salt so-obtained with thionyl chloride to yield an acyl chloride having the general formula I in which R represents a chlorine atom; reacting the acyl chloride so-obtained with a secondary amine to yield an amide having general formula I in which R represents a secondary amino group; and reacting the amide so-obtained with an organometallic reagent to yield the ketone having general formula I.

8 Claims, 2 Drawing Sheets

PROCESS FOR PREPARING 1,3-DIOXOLANE KETONES

The present invention relates to a process for the preparation of 1,3-dioxolane ketones, in particular 2,2-disubstituted 1,3-dioxolane ketones.

(R)-2,2-dimenthyl-1,3-dioxolane-4-methanol is an important starting material for the preparation of agricultural and pharmaceutical products; see, for example, Jurczak et al, Tetrahedron 42 (2) (1986) 447–488. An effective microbiological process for the preparation of the R-isomer is described and claimed in EP-A-0244912.

Homochiral 2-hydroxy-acids constitute one of the most important kinds of compounds used in asymmetric synthesis, either as building blocks or as chiral auxiliaries; see "Asymmetric Synthesis" Vol. IV, ed. Morrison and Scott (1984). A precursor of such an acid is 2,3-0-isopropylideneglyceric acid which is an oxidised derivative of 2,2-dimethyl-1,3-dioxolane-4-methanol.

Baer, Biochem. Prep. 2 (1952) 31, discloses that another oxidised analogue of 2,2-dimethyl-1,3-dioxolane-4-methanol, that is (R)-(+)-glycer-aldehyde acetonide is available from D-mannitol. In a total synthesis of a pheromone, Mori, Tetrahedron 32 (1976) 1979-1981, discloses addition of the Grignard reagent MeMgI to the chiral aldehyde to give an epimeric mixture of the alcohols (in 42% yield), contaminated with two unidentified minor products. This crude mixture was oxidised with Jones reagent to give the corresponding methyl ketone in 44% yield (18% overall yield from the aldehyde).

A mixture of enantiomeric methyl ketones of 2,2-dimethyl-1,3-dioxolane-4-methanol is also disclosed by Hagen et al, Tetrahedron 35 (1979) 2583-2589, by reaction of the corresponding aldehyde with diazomethane, at a yield of about 60%. As reported by Hagen et al, Tetrahedron 36 1980 3101-3105, further reaction with diazomethane yields homologous ketones, in particular the ethyl and n-propyl ketones.

The value of any intermediate is enhanced if it can be processed by reactions giving high yields. The value of a homochiral intermediate is greatest if it can be processed by reactions which conserve its chirality, thereby avoiding the need for separation of enantiomers.

M. Larcheveque and Y. Petit, Synthesis 1986, pages 60 to 64, disclose a process for the preparation of ketones equivalent to 2,2-dimethyl-1,3-dioxolane-4-methanol from the corresponding dimethylamide by reaction with an appropriate organo magnesium compound. The dimethyl amide is prepared by reaction of the methyl ketone of 2,2-dimethyl-1,3-dioxolane-4-methanol with dry dimethylamine in methanol.

Most surprisingly, it has been found possible to prepare ketones of 2,2-disubstituted-1,3-dioxolane from the corresponding carboxylic acid in a multistage process incorporating a novel step for the preparation of an acyl chloride from a carboxylic acid, without the need to prepare an alkyl ketone as intermediate.

Accordingly, the present invention provides a process for preparing a ketone of the general formula:

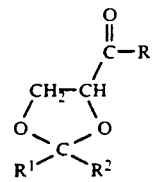

in which $R^1$ and $R^2$ each independantly represent a $C_{1-6}$ alkyl or $C_{6-12}$ aryl group, and R represents an alkyl, aryl, aralkyl, heterocyclic or carboxylic group, which process comprises reacting a carboxylic acid having the general formula I in which R represents a hydroxy group with a lithium compound to form the corresponding lithium salt of the carboxylic acid; reacting the lithium salt so-obtained with thionyl chloride to yield an acyl chloride having the general formula I in which R represents a chlorine atom; reacting the acyl chloride so-obtained with a secondary amine to yield an amide having general formula I in which R represents a secondary amino group; and reacting the amide so-obtained with an organometallic reagent to yield the ketone having general formula I.

Figure 1:
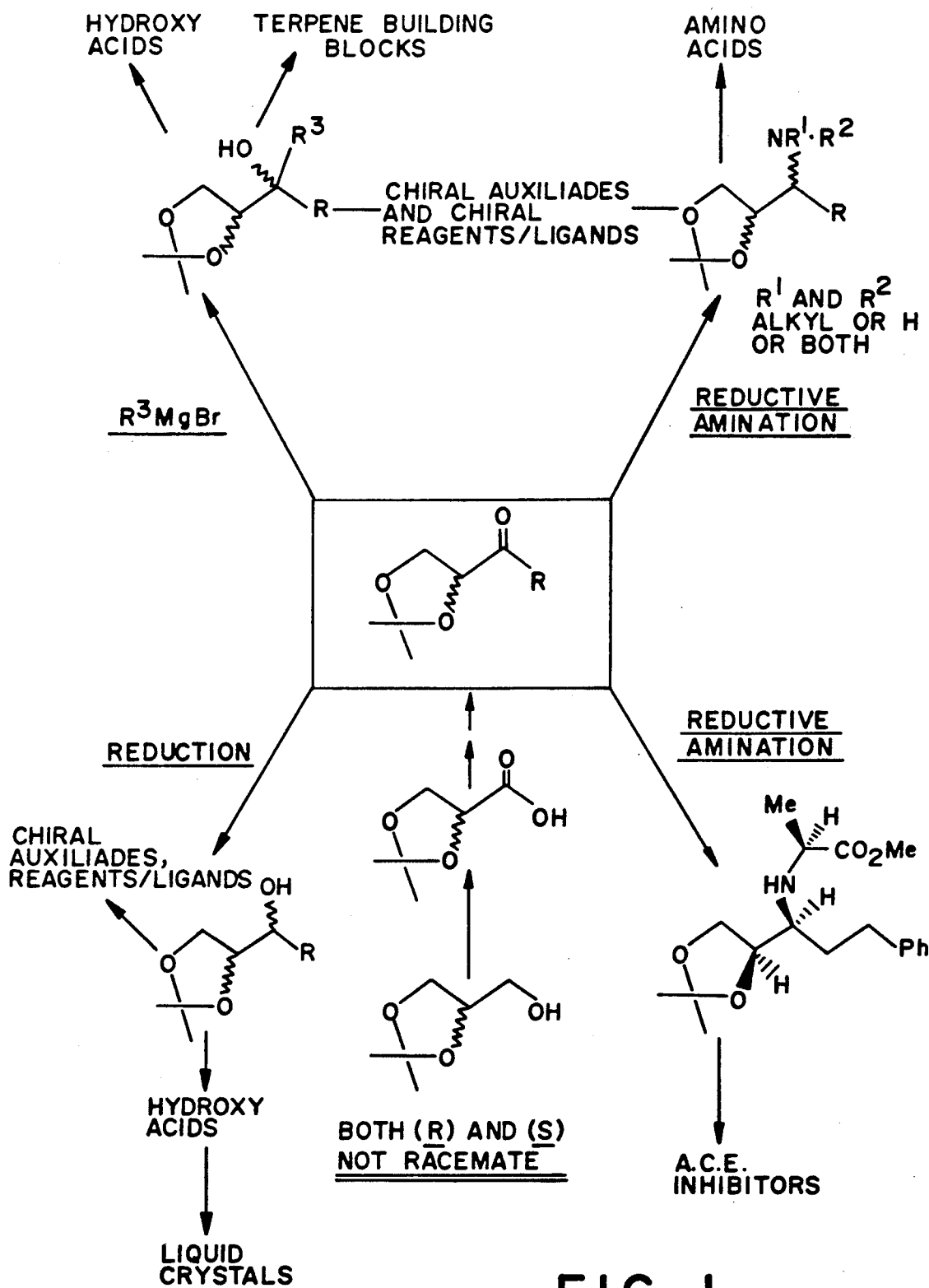
FIG. 1 depicts various method of use of ketone compounds of the present invention.

Alkyl groups present in the compounds employed in the process of the present invention may be straight chain or branched.

$R^1$ and $R^2$ preferably each independantly represent a $C_{1-6}$ alkyl group, more preferably a $C_{1-4}$ alkyl group. $R^1$ and $R^2$ are both preferably methyl.

R preferably represents a $C_{1-6}$ alkyl group, more preferably a $C_{1-3}$ alkyl group, especially methyl or propyl; phenyl; a phenalkyl, especially phenyl-substituted ethyl; or cyclohexyl.

Groups represented by R, $R^1$ and $R^2$ may, optionally, bear one or more substituents. Optional substituents may be selected from those groups typical in the art, for example halogen atoms and alkyl, alkenyl, alkynyl, alkoxy, alkylthio, cyano and nitro groups.

The process according to the present invention gives products in high yields without loss of chirality. The novel reaction for preparing acyl chlorides is particularly suitable in cases where the corresponding carboxylic acid does not give the acyl chloride on reaction with thionyl chloride. Thus, if the carboxylic acid starting material of the process of the present invention is reacted directly with thionyl chloride, it has been found that the product is not the corresponding acid chloride, but rather a compound having the general formula:

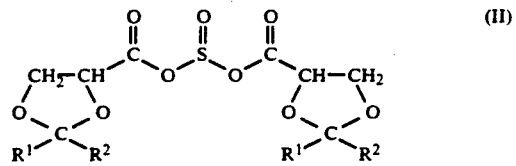

in which $R^1$ and $R^2$ are as hereinbefore defined. Although the compound of formula II may be a valuable intermediate in preparation of homochirons, the novel multi-step process via the lithium salt provides the acid chloride in high yield.

In the first step, the carboxylic acid is reacted with a lithium compound, such as lithium hydride or lithium hydroxide, to yield the salt of the carboxylic acid. The reaction is conveniently conducted in an anhydrous solvent such as ethylene glycol dimethyl ether, under an inert atmosphere whilst heating under reflux.

In the second step, the lithium salt is reacted with thionyl chloride, in an anhydrous solvent, such as dichloromethane, under an inert atmosphere, at room temperature or below. A convenient temperature for this step is 0° C. The product of the second step of the process is an acyl chloride.

The conversion of the acyl chloride to the corresponding amide may be conducted by techniques known in the art, for example, by reaction of the acyl chloride with a suitable secondary amine in the presence of an inert solvent, for example pyridine or triethylamine/dichloroethane, for a period of 2 to 3 hours. The reaction is typically performed at a temperature of from 0° to 20° C. The secondary amine may be present as the amine itself or as a salt, for example the hydrohalide salt.

For the conversion of the amide to the corresponding ketone, an organometallic reagent, for example a Grignard reagent, RMgX, or lithium reagent, RLi, is chosen having regard to the nature of R as hereinbefore defined. The reaction is conducted under conditions well known in the art, for example in the presence of an inert solvent, such as tetrahydrofaran, typically for a period of up to about 1 hour at a temperature of about 0° C.

The literature suggests that the amide of the process must be present as an O-alkylamide, for example the O-methylamide, in order to stabilise the intermediate formed during reaction with a Grignard reagent, and hence suppress over-addition of the Grignard reagent. Although the O-alkylamide can be used with success, N,O-dialkylhydroxylamine salts, for example the hydrochlorides, are expensive reagents. Surprisingly, it has been found that the cheaper N,N-dialkylamides, for example N,N-dimethylamide, can be converted to a range of ketones, although these have previously only been suggested as adequate for the preparation of simple ketones. As will be seen from the Examples below, a variety of ketones has been synthesised in good yields from the dimethylamide.

The carboxylic acid starting materials for the process of the present invention may be prepared by oxidation of the corresponding alcohol, that is a compound having the general formula

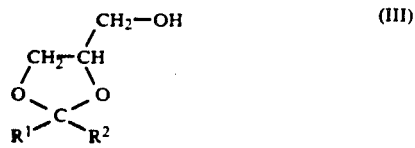

in which $R^1$ and $R^2$ are as hereinbefore defined. The oxidation may conveniently be performed by reaction of the compound of formula III with potassium permanganate and sodium hydroxide in aqueous solution for a period of 4 to 5 hours, at a temperature of about 0° C.

As indicated above, the reactions described herein do not give racemisation. If the starting material is in the form of a racemic mixture, the product is also in this form, but the present invention allows an enantiomer having a desired configuration to be prepared. Thus, starting materials for the process for the present invention are preferably present in predominantly one enantiomeric form.

The ketones of formula I can be used to generate secondary and further homochiral centres. By way of example, the ketones may be converted to olefins, by Wittig reactions, or converted to enolates which can be subjected to alkylation, aldol condensation or epoxidation without loss of chirality, and the introduction of new homochiral centres. Homochiral compounds can be prepared, for asymmetric chemical synthesis, and it is particularly desirable that such compounds are highly pure. Compounds produced by the process of the invention thus have utility as homochiral synthons, as enantioselective reagents, and in asymmetric synthesis. FIG. 1 indicates various utilities of the ketones.

An advantage of the ketones of formula I has been found in that, when reduced (thereby generating a second chiral centre), there can be a considerable degree of diastereoselective reduction of the carbonyl group, while using simple reducing agents. This can be illustrated with respect to FIG. 2 which also shows how ketones of formula I may be converted to useful products.

Figure 2:
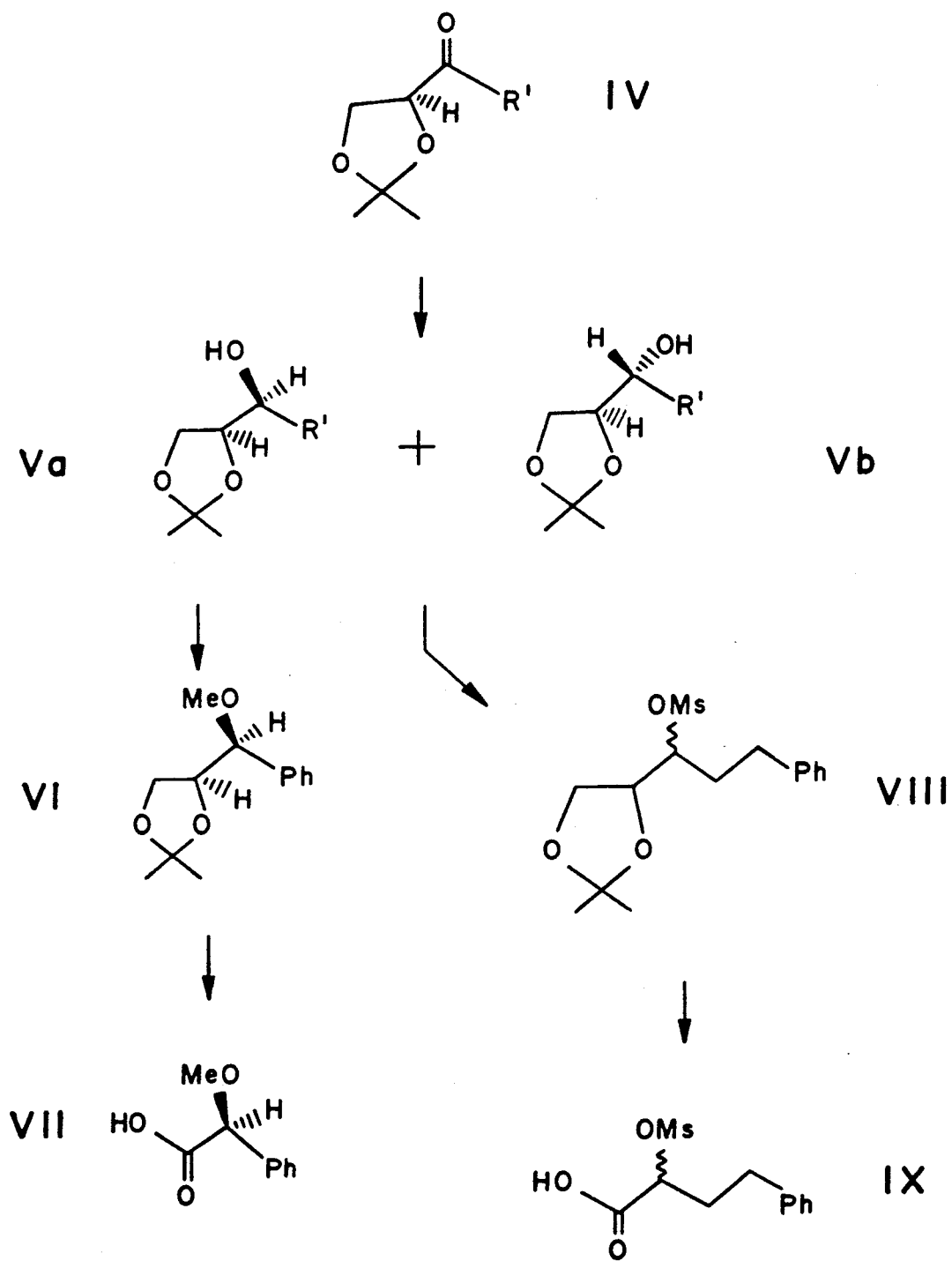
FIG. 2 depicts the conversion of ketones of formula I to useful products.

If the compound of formula IV of FIG. 2 in which R' is phenyl or phenethyl is reduced with DIBAL-H, for example in tetrahydrofuran at −78° C. for 1 hour, a mixture of compounds of formulae Va and Vb of FIG. 2 is obtained in high or even quantitative yield. When R' is phenyl, the compound Va:compound Vb ratio is 3.5:1, and when R' is phenylethyl, the compound Va:compound Vb ratio is 18:1. Depending on the nature of R', therefore, or indeed on the solvent and other reaction conditions, a high degree of diastereoselectivity can be achieved.

When R' is phenyl, the diastereoisomers can be readily separated, and the compound of formula Va in FIG. 2 converted to that of formula VI by a two-step reaction, first with sodium hydride, for example in tetrahydrofuran at 60° C. for 2-3 hours, the second with methyliodide, for example at about 40° C. for 2-3 hours. The yield is quantitative. (S)-O-methylmandelic acid (compound VIII in FIG. 2) is obtained in high yield by reaction of compound VI with mineral acid in tetrahydrofuran followed by oxidation with ruthenium tetroxide, at room temperature. (R)- and (S)-O-methylmandelic acid are useful reagents, intermediates and resolving agents.

When R' is phenylethyl, the compound Va/compound Vb mixture (18:1) is not easily separated. By reaction of the mixture with mesyl chloride in an inert solvent, a mixture of diasterioisomers of formula VIII is obtained; if that mixture is reacted with mineral acid and then with ruthenium tetroxide, the compound of formula IX in FIG. 2 is obtained and can be separated. The product is useful as an intermediate in the preparation of ACE (angiotensin-converting enzyme) inhibitors.

The following examples 2 to 10 illustrate how compounds of the invention may be prepared. Example 1 illustrates the preparation of a starting material from the known alcohol (R)-2,2-dimethyl-1,3-dioxolane-4-methanol (formula V in FIG. 2).

The (R)-alcohol had an optical purity of >99.5% and a chemical purity of about 96%. The chirality of the product of each Example was checked by chiral g.l.c. against the standard resolved racemates.

EXAMPLE 1

Preparation of (S)-(+)-2,3-O-isopropylideneglyceric acid

To a stirred and cooled (0°-5° C.) solution of the (R)-alcohol (52.8 g, 0.4 mol) in aqueous sodium hydroxide (16 g, 0.4 mol, in 1.5 l distilled water), potassium permanganate (96 g, 0.6 mol) was added portionwise over 1.75-2 h. The reaction temperature was maintained below 10° C. during the addition. A further portion of potassium permanganate (10 g, 0.6 mol, in distilled water) (250 ml) was then added over a further 0.5 h. The reaction mixture was stirred at 0°-5° C. for a further 1 h and the resultant mixture filtered. The residue was washed with water (3×150 ml) and the washings combined with the main filtrate. The combined aqueous filtrate was acidified with hydrochloric acid to pH 2.0, saturated with sodium chloride and extracted with ether (6×500 ml), maintaining the temperature below 15° C. The combined extracts were dried (MgSO$_4$) and filtered, and the filtrate was evaporated in vacuo to give the title compound as a pale yellow oil (36.3 g, 62.2%). This was used without purification.

EXAMPLE 2

Preparation of (S)-(+)-2,3-O-isopropylideneglyceric acid lithium salt

To a stirred solution of the (S)-acid of Example 1 (29.2 g, 0.2 mol) in ethylene glycol dimethyl ether (anhydrous, 800 ml) under nitrogen was added finely ground lithium hydride (1.8 g, 0.22 mol). The stirred mixture was refluxed gently for 24 h, then cooled and evaporated in vacuo. Anhydrous ether (150 ml) was added and the product filtered off. The product was then washed with 4×150 ml portions of anhydrous ether, and then dried in vacuo over potassium hydroxide pellets to give the title compound as a crisp white solid (27.2 g, 89.5%) which was used without purification.

EXAMPLE 3

Preparation of (S)-(+)-2,3-O-isopropylideneglycinoyl chloride

To a stirred and cooled (0°-5° C.) solution of thionyl chloride (8.8 g, 5.4 ml, 0.074 mol) in anhydrous dichloromethane (90 ml), the lithium salt of Example 2 (10.2 g, 0.067 mol) was added portionwise over 10 min and under nitrogen. The temperature was allowed to rise to room temperature over 60 min and the mixture was stirred for a further 3 h. The precipitated lithium chloride was removed by filtration and washed with 3×50 ml portions of anhydrous ether. The washings were added to the main filtrate, and the combined solution was evaporated in vacuo at 30°-40° C. to give the title compound as a pale yellow oil (10.45 g, 94.8%). This material was stored under nitrogen at −20° C. and used without purification.

EXAMPLE 4

Preparation of (S)-(+)-N,N-dimethyl-2,3-O-isopropylideneglyceramide

To a stirred and cooled (0°-5° C.) solution of thionyl chloride (5.6 ml, 0.077 mol) in anhydrous dichloromethane (90 ml) under nitrogen was added the lithium salt of Example 2 (9.4 g, 0.062 mol) over 10 min. The mixture was stirred at room temperature for 3 h, then the precipitated lithium chloride was removed by filtration and washed with 3×20 ml portions of anhydrous dichloromethane. The washes were added to the main filtrate and the resultant solution was evaporated to a volume of approximately 80 ml. To this cooled (0°-5° C.) solution was added dimethylammonium hydrochloride (5.5 g, 0.068 mol), followed by the dropwise addition over 15-20 min of anhydrous pyridine (12.4 ml, 0.155 mol). The reaction mixture was stirred at 0°-10° C. for 1 h, then washed with water (3×20 ml), dried (MgSO$_4$) and evaporated to give the title compound as a pale orange oil (9.0 g, 84%): [a]$^{20}$D= =3.6° (cl, EtOH). This material was used without purification.

EXAMPLE 5

Preparation of (S)-(+)-N-methoxy,N-methyl-2,3-O-isopropylideneglyceramide

To a stirred and cooled (0°-5° C.) solution of thionyl chloride (0.9 ml, 0.0125 mol) in anhydrous dichloromethane (15 ml), the lithium salt of Example 2 (1.52 g, 0.01 mol) was added portionwise over 5 min and under nitrogen. The cooling bath was removed and the reaction mixture stirred at room temperature for 3 h. The precipitated lithium chloride was removed by filtration and washed with anhydrous dichloromethane (15 ml). The washings were added to the main filtrate and the combined solution was evaporated to a volume of 20 ml. To this cooled (0°-520 C.) and stirred solution, under nitrogen, was added N,O-dimethylhydroxylamine hydrochloride (1.1 g, 0.011 mol), followed by the dropwise addition, over 5 min, of anhydrous pyridine (2.0 ml, 0.025 mol). The resultant mixture was stirred at 0°-10° C. for 1 h, then diluted with methylene chloride (30 ml) and washed with saturated sodium chloride solution (2×10 ml). The organic solution was dried (MgSO$_4$) and evaporated to give the title compound (1.8 g, 95%). This material was used without purification.

EXAMPLE 6

Preparation of (S)-(−)-1,2-dihydroxy-(1,2-O-isopropylidene)-butan-3-one

To a rapidly stirred and cooled (0° C.) solution of the amide of Example 4 (0.692 g, 4 mmol) in dry THF (10 ml), methyl magnesium chloride (1.5 ml of 3 M solution in THF, 4.4 mmol) was added over 10-15 min. The reaction was stirred for a further 1 h at 0° C. and then quenched by pouring it rapidly into vigorously-stirred saturated ammonium chloride solution (ca.50 ml). This was stirred for 10 min and then extracted with dichloromethane (3×20 ml). The extracts were dried (MgSO$_4$) and evaporated under reduced pressure to give the crude product as a colourless oil (310 mg, 54%):[a]$^{20}$D= −65.8° (cl, EtOH). The low yield was undoubtedly due to loss during evaporation. The material obtained was 98% pure by g.l.c.

EXAMPLE 7

Preparation of (S)-(−)-1,2-dihydroxy-(1,2-O-isooropylidene)-4-methylpentan-3-one The procedure of Example 6 was repeated, but using only 2 mmol of the amide and, as the Grignard reagent, 2.2 mmol isopropylmagnesium chloride (2 M solution in THF). The title product was obtained as a colourless oil (0.285 g, 83%):[a]²⁰D = −78.3° (cl, EtOH); purity >97% by g.l.c.

EXAMPLE 8

Preparation of (S)-(−)-1,2-dihydroxy-(1,2-O-isopropylidene)-3-cyclohexylpropan-3-one The procedure of Example 6 was repeated, but using 4.4 mmol isopropylmagnesium chloride (2 M solution in THF). The title product was obtained as a colourless oil (0.285 g, 83%):[a]²⁰D = −51.4° (cl, EtOH).

EXAMPLE 9

Preparation of (S)-(−)-1,2-dihydroxy-(1,2-O-isopropylidene)-3-phenylpropan-3-one The procedure of Example 6 was repeated, but using 18.52 mmol amide and, as the Grignard reagent, 22.2 mmol phenylmagnesium chloride (2 M solution in THF) added over a 20 min period. The crude product was obtained as a pale yellow crystalline solid (3.7415 g, 98%). This was recrystallised from petrol/ether, to give the title compound as very pale yellow crystals (3.45 g, 90% yield); m.pt. 57°-59° C.; [a]²⁰D = −4.2° (cl, EtOH); purity >98% by g.l.c.

EXAMPLE 10

Preparation of (S)-(−)-1,2-dihydroxy-(1,2-O-isopropylidene)-5-phenylpentan-3-one The procedure of Example 6 was repeated, but using 50 mmol amide and, as the Grignard reagent, 60 mmol phenethylmagnesium bromide (1 M solution in THF). The title product was obtained as a yellow oil (11.2 g, 96%): [a]²⁰D = −32.4° (cl, EtOH).

We claim:

1. A process for preparing a ketone of the formula:

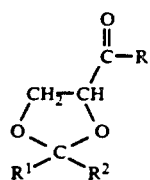

in which $R^1$ and $R^2$ each independently represent a $C_{1-6}$ alkyl or $C_{6-12}$ aryl group, and R represents alkyl, aryl, cyclohexyl, or aralkyl, which process comprises the steps of:

reacting a carboxylic acid having the following formula in which $R^1$ and $R_2$ are as hereinbefore defined:

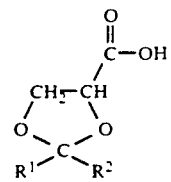

with a lithium compound selected from the group consisting of lithium hydride and lithium hydroxide to form the corresponding lithium salt of the carboxylic acid;

reacting the lithium salt so-obtained with thionyl chloride to yield an acyl chloride having the following formula in which $R^1$ and $R_2$ are as hereinbefore defined:

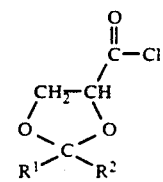

reacting the acyl chloride so-obtained with a secondary amine to yield an amide having the following formula in which $R^3$ represents a secondary amino group, and $R^1$ and $R^2$ are as hereinbefore defined:

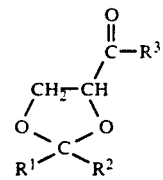

and, reacting the amide so-obtained with an organometallic reagent selected from the group consisting of Grignard and lithium reagents to yield the ketone having formula I.

2. A process according to claim 1, characterised in that the carboxylic acid is in the form of a single enantiomer.

3. A process according to claim 1, characterised in that the secondary amine is a dialkylamine or a N,O-dialkylhydroxylamine.

4. A process according to claim 3, characterised in that the secondary amine is dimethylamine.

5. A process according to claim 1, characterised in that the organometallic reagent is an organo magnesium compound.

6. A process according to claim 1, characterised in that R represents $C_{1-3}$ alkyl phenyl, phenalkyl or cyclohexyl.

7. A process according to claim 1, characterised in that $R^1$ and $R^2$ independantly represent a $C_{1-6}$ alkyl group.

8. A process according to claim 1, characterised in that the carboxylic acid is prepared by oxidation of a compound having the formula

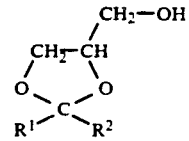

(III)

in which $R^1$ and $R^2$ are as defined in claim 1.

* * * * *